United States Patent [19]

Arima et al.

[11] Patent Number: 4,979,133
[45] Date of Patent: Dec. 18, 1990

[54] PYROMETER

[75] Inventors: Jiro Arima; Hiroji Tsujimura, both of Osaka, Japan

[73] Assignee: Minolta Camera Kabushiki Kaisha, Osaka, Japan

[21] Appl. No.: 308,432

[22] Filed: Feb. 8, 1989

[30] Foreign Application Priority Data

Feb. 8, 1988 [JP] Japan .................................. 63-27299

[51] Int. Cl.$^5$ .............................................. G01J 5/00
[52] U.S. Cl. ................................... 364/557; 374/121; 250/338.1; 356/45
[58] Field of Search ............... 364/557, 555, 525, 550, 364/556; 356/43, 45, 48; 374/120, 121, 126, 129, 130, 133; 250/338.1, 339

[56] References Cited

U.S. PATENT DOCUMENTS

| | | | |
|---|---|---|---|
| 4,411,519 | 10/1983 | Tagami ................................. | 356/45 |
| 4,647,774 | 3/1987 | Brisk et al. ........................ | 250/338.1 |
| 4,657,385 | 4/1987 | Pointer ................................ | 356/43 |
| 4,679,934 | 7/1987 | Ganguly et al. ..................... | 356/43 |
| 4,708,493 | 11/1987 | Stein ................................... | 374/128 |
| 4,797,840 | 1/1989 | Fraden ............................... | 364/557 |
| 4,823,291 | 4/1989 | Berman .............................. | 364/557 |
| 4,859,065 | 8/1989 | Bibby ................................. | 356/45 |

FOREIGN PATENT DOCUMENTS

| | | |
|---|---|---|
| 56-130622 | 10/1981 | Japan . |
| 56-130623 | 10/1981 | Japan . |
| 38627 | 2/1985 | Japan .................................. 374/121 |
| 60-54936 | 4/1985 | Japan . |
| 60-54937 | 4/1985 | Japan . |
| 61-30727 | 2/1986 | Japan . |
| 61-86621 | 5/1986 | Japan . |
| 61-29647 | 7/1986 | Japan . |
| 1213738 | 9/1986 | Japan .................................. 374/121 |
| 62-1202 | 1/1987 | Japan . |
| 62-15424 | 1/1987 | Japan . |

OTHER PUBLICATIONS

Applied Optics, R. J. Brown, B. G. Young, Dec. 1975, vol. 14, No. 12, pp. 2927-2934.

Primary Examiner—Kevin J. Teska
Assistant Examiner—Michael Zanelli
Attorney, Agent, or Firm—Price, Gess & Ubell

[57] ABSTRACT

A pyrometer according to the present invention calculates a temperature of a target to be measured by means of light emitting device for emitting reference light having three wavelengths to the target, and light measuring portions for measuring the intensity of the reference light, the intensity of light reflected by the target, the intensity of light transmitted through the target and the intensity of light radiated by the target, respectively with respect to each of the three wavelengths. The transmitted light measured value of the reference light transmitted through the target is used for temperature calculation in addition to the measured values of the reference light, the reflected light and the radiated light, and therefore even if the target is a semi-transparent object, the true temperature thereof can be calculated.

12 Claims, 2 Drawing Sheets

PYROMETER

BACKGROUND OF THE INVENTION

1. Field of the Invention

The present invention relates to a pyrometer, more particularly, it relates to a pyrometer for measuring the temperature of a target by employing light as a medium.

2. Description of the Prior Art

In such a pyrometer, it is necessary to know the emissivity of a target to be measured, but in general, such emissivity can not be known. Therefore, in a plurality of proposed pyrometers, the emissivities of a target to be measured are assumed as follows: In Japanese Laid-Open Patent Application No. 130622/1981, light having two different colors (two different wavelengths $\lambda_1$, $\lambda_2$) is measured, and the emissivity $\epsilon$ in the wavelength $\lambda_1$ is assumed to be equal to the emissivity $\epsilon$ in the wavelength $\lambda_2$. In the other Japanese Laid-Open Patent Application No. 130623/1981, light having three different colors (three different wavelengths) is measured, and the emissivities $\epsilon(\lambda)$ in respective wavelengths are assumed that $\epsilon(\lambda) = exp.(a_0 + a_1\lambda)$, wherein $a_0$ and $a_1$ represent constants respectively. Furthermore, in the U.S. Pat. No. 4,411,519, three temperatures $T_{12}$, $T_{23}$, and $T_{31}$ are calculated with assuming $\epsilon(\lambda_1) = \epsilon(\lambda_2)$, $\epsilon(\lambda_2) = \epsilon(\lambda_3)$, $\epsilon(\lambda_3) = \epsilon(\lambda_1)$ respectively, and a true temperature T is obtained by $T = (T_{12} + T_{23} + T_{31})/3$.

Meanwhile, in the other Japanese Laid-Open Patent Application No. 30727/1986, the intensities $L(\lambda_1)$ and $L(\lambda_2)$ of light reflected by the target are measured in two different wavelengths $\lambda_1$, $\lambda_2$ respectively, and the temperature is calculated on the basis of the measured light intensities $L(\lambda_1)$, $L(\lambda_2)$, and a reflected light intensity ratio $L(\lambda_1)/L(\lambda_2)$ represented by the emissivities $\epsilon(\lambda_1)$, $\epsilon(\lambda_2)$ as follows:

$$L(\lambda_1)/L(\lambda_2) = \{1 - \epsilon(\lambda_1)\}/\{1 - \epsilon(\lambda_2)\} \quad (A)$$

Namely, assuming that the measured radiation intensity in wavelength $\lambda$ is $D(\lambda)$ and the radiation intensity of blackbody in the wavelength $\lambda$ at temperature T is $D_0(\lambda, T)$, the following equation is established:

$$\epsilon(\lambda) = D(\lambda)/D_0(\lambda, T) \quad (B)$$

Here, the temperature T can be calculated in accordance with the equation (A), since the unknown factor is only T in the equation (A) if $\epsilon(\lambda)$ shown in the equation (B) is substituted to the equation (A). $D_0(\lambda, T)$ can be calculated in accordance with the well-known Planck formula and constants peculiar to the device.

However, in Japanese Laid-Open Patent Application Nos. 130622/1981 and 7529/1982, since it is assumed that $\epsilon(\lambda_1) = \epsilon(\lambda_2)$, the true temperature can be calculated only when a spectral characteristic of emissivity is constant. In other words, when the spectral characteristic of emissivity is not constant, assumption $\epsilon(\lambda_1) = \epsilon(\lambda_2)$ itself is erroneous, so that the true temperature can not be calculated. In either case, in Japanese Laid-Open Patent Application No. 130622/1981, U.S. Pat. No. 4,411,519 and including Japanese Laid-Open Patent Application No. 130623/1981, since information on the reflected light is not included in the assumption of an emissivity, the true temperature can not be obtained except in the case of constant spectral characteristic of emissivity.

On the other hand, in the calculation in Japanese Laid-Open Patent Application No. 30727/1986, there may be the case that two different temperatures are obtained. This is because that, the equation $R(\lambda_1)/R(\lambda_2) = \{1 - \epsilon(\lambda_1)\}/\{1 - \epsilon(\lambda_2)\}$, where R is a reflectance, used in the calculation is only established when all reflected light from the target to be measured are collected or it has a perfect diffusion surface.

Therefore, in a preceding U.S. patent application of Ser. No. 203,003, it is suggested to provide a pyrometer which is possible to calculate the true temperature even when the spectral characteristic of emissivity is not constant, by including measured reflection information.

However, a pyrometer disclosed in the aforesaid U.S. Patent application performs temperature measurement of a target on the premise that the target is a non-transparent object and is not directed to temperature measurement for a semi-transparent object. However, besides non-transparent objects, there are also present semi-transparent objects such as a semi-conductor wafer, ceramic (ceramic has a semi-transparent characteristic in the infrared region) and the like among objects whose temperatures are necessary to be measured. Accordingly, it has been desired to realize a pyrometer which is possible to calculate the temperature of such a semi-transparent object. And in this case, the emissivity of the semi-transparent object is necessary for temperature calculation.

SUMMARY OF THE INVENTION

Therefore, it is an object of the present invention to provide an emissivity measuring apparatus for measuring the emissivity of a target to be measured which is possible to calculate the emissivity of a semi-transparent target.

Another object of the present invention is to provide a pyrometer which is possible to calculate the true temperature of a semi-transparent target whose emissivity is unknown.

In order to achieve the aforesaid former object, an emissivity measuring apparatus for measuring an emissivity of a target to be measured according to the present invention comprises light emitting means for emitting reference light having at least three wavelengths to said target to be measured, first light measuring means for measuring the intensity of the reference light emitted by said light emitting means with respect to said at least three wavelengths to produce first signals, second light measuring means for measuring the intensity of light reflected by said target with respect to said at least three wavelengths to produce second signals, third light measuring means for measuring the intensity of light transmitted through said target with respect to said at least three wavelengths to produce third signals, fourth light measuring means for measuring the intensity of light radiated by said target with respect to said at least three wavelengths to produce fourth signals, and calculating means for calculating an emissivity $\epsilon(\lambda)$ of said target on the basis of a reference light measured value, a reflected light measured value, a transmitted light measured value and a radiated light measured value according to the first, second, third and the fourth signals respectively with respect to each of said at least three wavelengths.

The emissivity measuring apparatus thus constructed can give an emissivity effective for temperature calculation of a semi-transparent target.

Further, in order to achieve the latter object described above, a pyrometer according to the present invention comprises light emitting means for emitting reference light having at least three wavelengths to said target to be measured, first light measuring means for measuring the intensity of the reference light emitted by said light emitting means with respect to said at least three wavelengths to produce first signals, second light measuring means for measuring the intensity of light reflected by said target with respect to said at least three wavelengths to produce second signals, third light measuring means for measuring the intensity of light transmitted through said target with respect to said at least three wavelengths to produce third signals, fourth light measuring means for measuring the intensity of light radiated by said target with respect to said at least three wavelengths to produce fourth signals, and calculating means for calculating a temperature of said target on the basis of a reference light measured value, a reflected light measured value, a transmitted light measured value and a radiated light measured value according to the first, second, third and fourth signals respectively with respect to each of said at least three wavelengths.

According to the pyrometer thus constructed, the transmitted light of the reference light through the target having at least three different wavelengths is measured and the measured value thereof at each wavelength is used as data for temperature calculation in addition to the measured values of the reference light, the reflected light of the reference light reflected by the target and the radiated light from the target itself. Therefore, even if the target is a semi-transparent object, the temperature thereof can be calculated.

BRIEF DESCRIPTION OF THE DRAWINGS

These and other objects and features of the present invention will become apparent from the following description taken in conjunction with preferred embodiments thereof with reference to the accompanying drawings, throughout which like parts are designated by like reference numerals, and in which.

DETAILED DESCRIPTION OF THE PREFERRED EMBODIMENT

Figure 1:
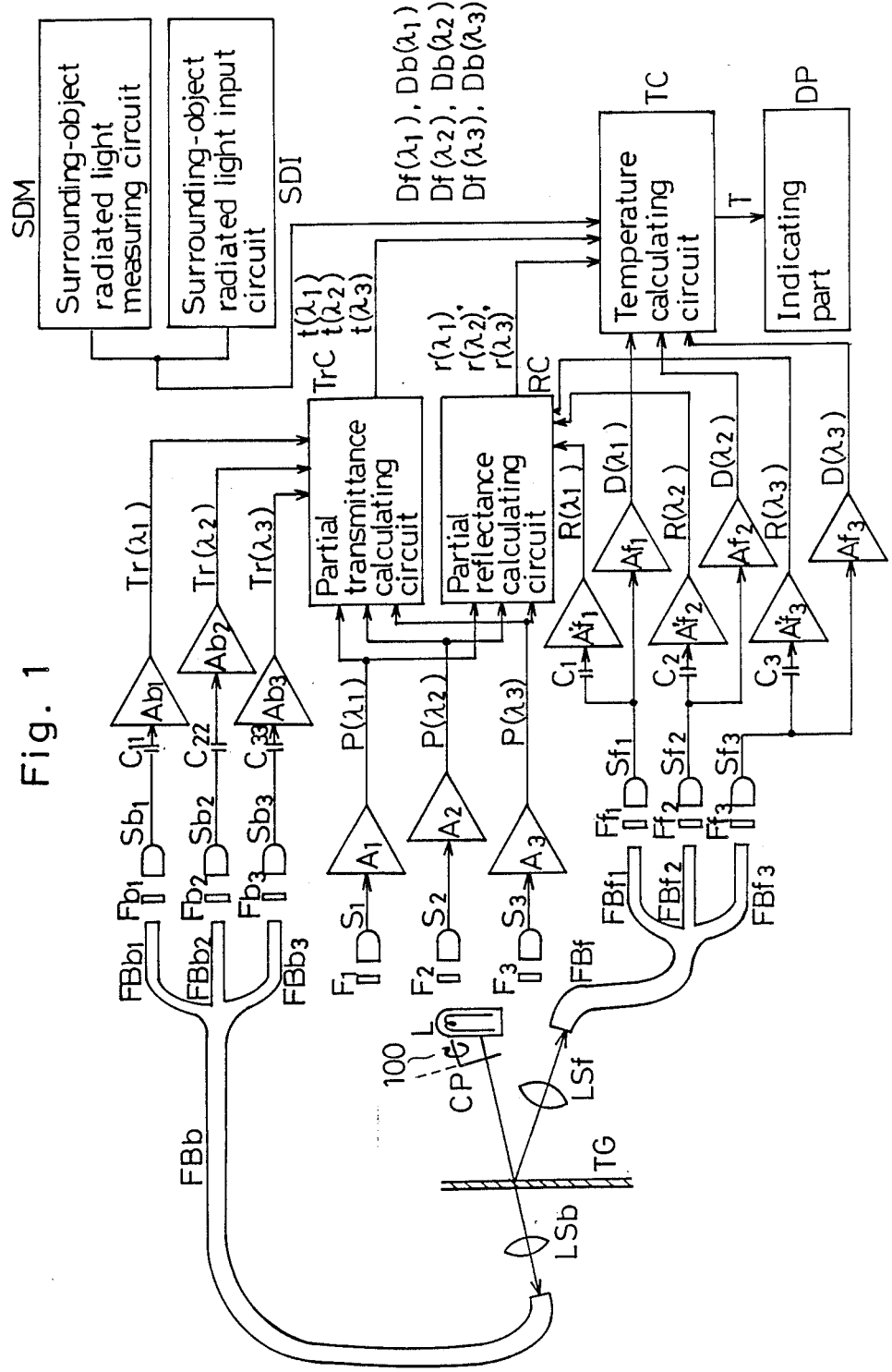
FIG. 1 is a schematic construction diagram of a pyrometer of one embodiment of the present invention.

One embodiment of the present invention will now be described in conjunction with the drawings. FIG. 1 is a schematic construction diagram of a pyrometer including an emissivity measuring apparatus of one embodiment of the present invention. In the present embodiment, light having three different wavelengths $\lambda_1$, $\lambda_2$, $\lambda_3$ will be measured. A light emitting device 100 comprises a light source L which produces reference light including the light having three different wavelengths $\lambda_1$, $\lambda_2$, $\lambda_3$ and a chopper CP which intermits the reference light from the light source L, and irradiates the intermittent light to a target TG. The chopper CP comprises a mechanism which rotates a rotor having light transmitting and interrupting portions. On the front side of the target TG, a lens LSf is provided which receives light radiated by the target TG itself and the reference light reflected by the target TG simultaneously and condenses them. The condensed light is transmitted and divided into three different optical paths by an optical fiber FBf and its branch portions FBf$_1$, FBf$_2$, FBf$_3$. The light transmitted through the branch portions FBf$_1$, FBf$_2$, FBf$_3$ are received respectively by optical detectors Sf$_1$, Sf$_2$, Sf$_3$ through optical filters Ff$_1$, Ff$_2$, Ff$_3$ which transmit light of predetermined wavelengths of $\lambda_1$, $\lambda_2$, $\lambda_3$ respectively. In the optical detectors Sf$_1$, Sf$_2$, Sf$_3$, both an intensity signal of the light radiated from the target TG itself on the front side and an intensity signal of the reflected light of the light source L reflected by the target TG are simultaneously detected in superposition. The radiation intensity of the light radiated from the target TG itself among output signals of the optical detectors Sf$_1$, Sf$_2$, Sf$_3$ is constant, so that it is detected as direct current (hereinafter referred to as DC) signals, and the detected DC signals are amplified by DC amplifiers Af$_1$, Af$_2$, Af$_3$ and outputted as radiated light measured values $D(\lambda_1)$, $D(\lambda_2)$, $D(\lambda_3)$ with respect to the wavelengths $\lambda_1$, $\lambda_2$, $\lambda_3$. The radiated light measuring means with respect to the three-wavelength light is constituted by the DC amplifiers Af$_1$, Af$_2$, Af$_3$, optical filters Ff$_1$, Ff$_2$, Ff$_3$ and optical detectors Sf$_1$, Sf$_2$, Sf$_3$.

Among output signals of the optical detectors Sf$_1$, Sf$_2$, Sf$_3$, the reflected light of the light source L reflected by the target TG is, since the light irradiated to the target TG from the light source L is modulated to intermittent light by the chopper CP, detected as alternating current (hereinafter referred to as AC) signals through coupling capacitors $C_1$, $C_2$, $C_3$ and the detected AC signals are amplified by AC amplifiers A'f$_1$, A'f$_2$, A'f$_3$, and outputted as reflected light measured values $R(\lambda_1)$, $R(\lambda_2)$, $R(\lambda_3)$ with respect to the wavelengths $\lambda_1$, $\lambda_2$, $\lambda_3$. The reflected light measuring means is constituted by the AC amplifiers A'f$_1$, A'f$_2$, A'f$_3$, optical filters Ff$_1$, Ff$_2$, Ff$_3$ and optical detectors Sf$_1$, Sf$_2$, Sf$_3$.

As similar to the front side, on the back side of the target TG, a lens LSb is provided which receives light radiated by the target TG itself and the reference light transmitted through the target TG simultaneously and condenses them. The condensed light is transmitted and divided into three different optical paths by an optical fiber FBb and its branch portions FBb$_1$, FBb$_2$, FBb$_3$. The light transmitted through the branch portions FBb$_1$, FBb$_2$, FBb$_3$ are received respectively by optical detectors Sb$_1$, Sb$_2$, Sb$_3$ through optical filters Fb$_1$, Fb$_2$, Fb$_3$ which transmit light of predetermined wavelengths of $\lambda_1$, $\lambda_2$, $\lambda_3$ respectively. In the optical detectors Sb$_1$, Sb$_2$, Sb$_3$, both an intensity signal of the light radiated from the target TG itself on the back side and an intensity signal of the transmitted light of the light source L transmitted through the target TG are simultaneously detected in superposition.

The transmitted light of the light source L transmitted through the target TG among output signals of the optical detectors Sb$_1$, Sb$_2$, Sb$_3$ is, since the light irradiated to the target TG from the light source L is modulated to intermittent light by the chopper CP, detected as AC signals through coupling capacitors $C_{11}$, $C_{22}$, $C_{33}$ and the detected AC signals are amplified by AC amplifiers Ab$_1$, Ab$_2$, Ab$_3$, and outputted as transmitted light measured values $Tr(\lambda_1)$, $Tr(\lambda_2)$, $Tr(\lambda_3)$ with respect to the wavelengths $\lambda_1$, $\lambda_2$, $\lambda_3$. The transmitted light measuring means is constituted by the AC amplifiers Ab$_1$, Ab$_2$, Ab$_3$, optical filters Fb$_1$, Fb$_2$, Fb$_3$ and optical detectors Sb$_1$, Sb$_2$, Sb$_3$.

Now, the intensity of the reference light with respect to the wavelengths $\lambda_1$, $\lambda_2$, $\lambda_3$ is necessary for calculating the reflectance and transmittance of the target, so that there are provided optical detectors $S_1$, $S_2$, $S_3$. The optical detectors $S_1$, $S_2$, $S_3$ are faced to the light source L through optical filters $F_1$, $F_2$, $F_3$ which transmit only the light corresponding to the wavelengths $\lambda_1$, $\lambda_2$, $\lambda_3$ respectively. Though the light source L emits light of various wavelengths, the optical detector $S_1$ detects therefrom the light intensity of wavelength component of $\lambda_1$ which is necessary for calculating the reflectance and transmittance of the target. Similarly, the optical detectors $S_2$, $S_3$ detect the light intensities of wavelength components of $\lambda_2$, $\lambda_3$ respectively. Detected outputs of the optical detectors $S_1$, $S_2$, $S_3$ are amplified respectively by DC amplifiers $A_1$, $A_2$, $A_3$ and outputted as reference light measured values $P(\lambda_1)$, $P(\lambda_2)$, $P(\lambda_3)$ with respect to the wavelengths $\lambda_1$, $\lambda_2$, $\lambda_3$. The reference light measuring means is constituted by the DC amplifiers $A_1$, $A_2$, $A_3$, optical filters $F_1$, $F_2$, $F_3$ and optical detectors $S_1$, $S_2$, $S_3$. The output signals $R(\lambda_1)$, $R(\lambda_2)$, $R(\lambda_3)$ of the AC amplifiers $A'f_1$, $A'f_2$, $A'f_3$ and output signals $P(\lambda_1)$, $P(\lambda_2)$, $P(\lambda_3)$ of the DC amplifiers $A_1$, $A_2$, $A_3$ are inputted to a partial reflectance calculating circuit RC, and the partial reflectance $r(\lambda_1)=R(\lambda_1)/P(\lambda_1)$ of the target TG at wavelength $\lambda_1$ and the partial reflectances $r(\lambda_2)=R(\lambda_2)/P(\lambda_2)$, $r(\lambda_3)=R(\lambda_3)/P(\lambda_3)$ of the target TG at wavelengths $\lambda_2$, $\lambda_3$ are calculated respectively. Similarly, the output signals $Tr(\lambda_1)$, $Tr(\lambda_2)$, $Tr(\lambda_3)$ of the AC amplifiers $Ab_1$, $Ab_2$, $Ab_3$ and output signals $P(\lambda_1)$, $P(\lambda_2)$, $P(\lambda_3)$ of the DC amplifiers $A_1$, $A_2$, $A_3$ are inputted to a partial transmittance calculating circuit TrC, and the partial transmittance $t(\lambda_1)=Tr(\lambda_1)/P(\lambda_1)$ of the target TG at wavelength $\lambda_1$, and the partial transmittances $t(\lambda_2)=Tr(\lambda_2)/P(\lambda_2)$, $t(\lambda_3)=Tr(\lambda_3)/P(\lambda_3)$ of the target TG at wavelengths $\lambda_2$, $\lambda_3$ are calculated respectively.

In the radiated light measured values $D(\lambda_1)$, $D(\lambda_2)$, $D(\lambda_3)$, two components of other light are also included that are the radiated light from a front-side surrounding object reflected by the target TG and the transmitted light of the radiated light from a back-side surrounding object transmitted through the target TG. Though the radiated light of surrounding objects may be neglected in the case where the temperatures thereof are adequately low compared with that of the target TG, there are provided surrounding-object radiated light measuring circuit SDM and surrounding-object radiated light input circuit SDI for the case where the radiated light of surrounding objects must be taken into consideration. When the surrounding-object radiated light value (or, the temperature and emissivity of the surrounding object) is known, it is inputted from the surrounding-object radiated light input circuit SDI to a temperature calculating circuit TC. If not, it can be measured by the surrounding-object radiated light measuring circuit SDM and in this case the temperature and emissivity are not necessary.

The outputs $r(\lambda_1)$, $r(\lambda_2)$, $r(\lambda_3)$ of the partial reflectance calculating circuit RC, outputs $t(\lambda_1)$, $t(\lambda_2)$, $t(\lambda_3)$ of the partial transmittance calculating circuit TrC, radiated light measured values $D(\lambda_1)$, $D(\lambda_2)$, $D(\lambda_3)$ obtained from the DC amplifiers $Af_1$, $Af_2$, $Af_3$, and the output of the surrounding-object radiated light measuring circuit SDM or the surrounding-object radiated light input circuit SDI are inputted to the temperature calculating circuit TC, and the true temperature of the target is calculated. With the result of the calculation, temerature T is indicated in an indicating part DP. The output of the surrounding-object radiated light measuring circuit SDM or the surrounding-object radiated light input circuit SDI comprises front-side surrounding-object radiated light values $Df(\lambda_1)$, $Df(\lambda_2)$, $Df(\lambda_3)$ and back-side surrounding-object radiated light values $Db(\lambda_1)$, $Db(\lambda_2)$, $Db(\lambda_3)$.

A method of calculating the true temperature from these data will be explained hereinbelow.

When a target to be measured is a blackbody, a light flux radiated per unit area, unit solid angle and unit wavelength from the target, that is to say, a spectral radiation intensity $L(\lambda, T)$ can be given by Planck formula. If the optical system of a measuring apparatus has a measuring area $\Delta A$ and measuring solid angle $\Delta \omega$, a radiated light measured value $Do(\lambda, T)$ is represented by using polar coordinates $(r, \theta, \phi)$ as follows:

$$Do(\lambda, T) = \alpha \cdot \Delta A \int_\lambda \int \int_{\Delta\omega} S(\lambda) \cdot L(\lambda, T) \cos\theta \sin\theta d\theta d\phi d\lambda \quad (1)$$

wherein, $S(\lambda)$ represents an overall spectral sensitivity of the optical detectors and optical filters, and $\alpha$ represents a constant determined by the measuring device, more specifically decided by a calibration measurement. Thus, the radiated light measured value $Do(\lambda, T)$ in the case of measuring the blackbody at the temperature T can be prepared. Generally, when an emissivity of the target to be measured is $\epsilon(\lambda, T)$, a radiated light measured value $D(\lambda, T)$ thereof having the wavelength $\lambda$ at the temperature T is represented as the following equation:

$$D(\lambda, T) = \epsilon(\lambda, T) \times Do(\lambda, T) \quad (2)$$

Next, the case where the target is a sufficiently thin semi-transparent object (the temperature distribution in the direction of thickness can be out of consideration) will be explained. Incident light is reflected, transmitted and absorbed by the target, and therefore when a reflectance is $\rho(\lambda)$, transmittance is $\tau(\lambda)$ and absorbance is $\alpha(\lambda)$, $$\rho(\lambda) + \tau(\lambda) + \alpha(\lambda) = 1 \quad (3)$$

is established.

Figure 2:
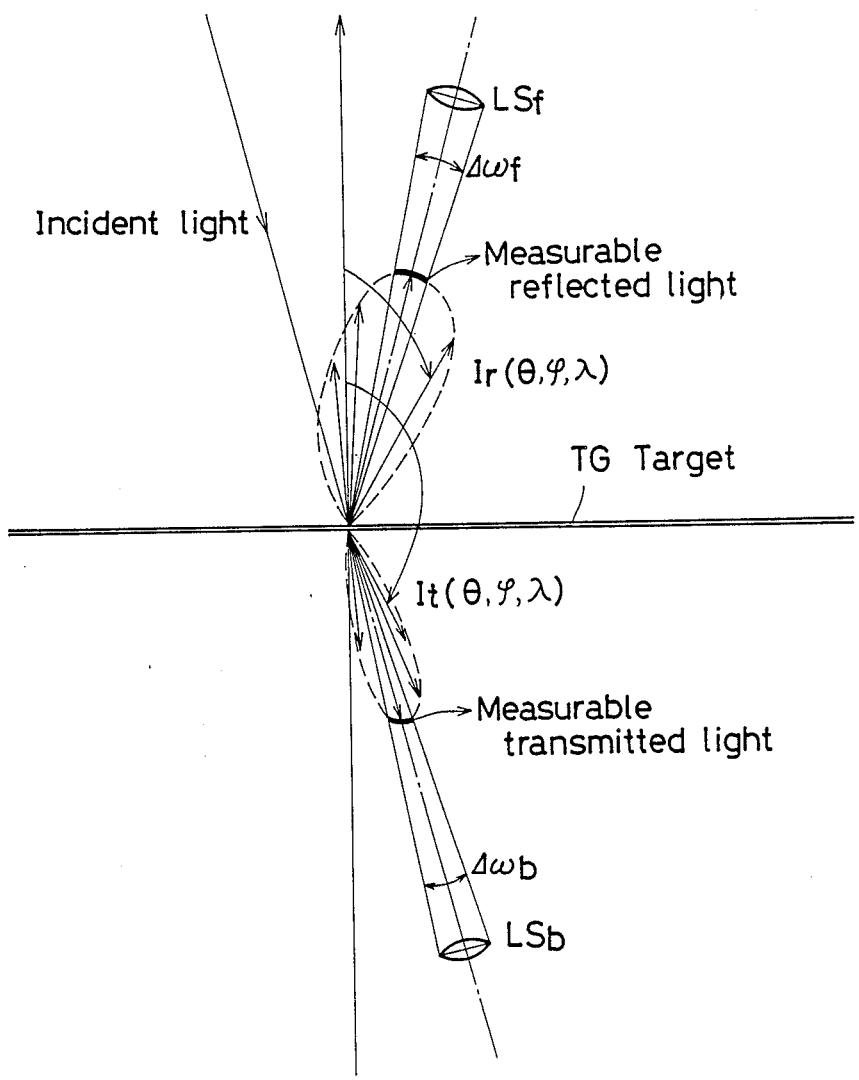
FIG. 2 is an explanatory view with respect to a reflectance and transmittance.

As shown in FIG. 2, when a beam of light of wavelength $\lambda$ having an unit light intensity is incident to the target TG, and the incident light is reflected and transmitted in various angles $(\theta, \phi)$ at the light intensities $Ir(\theta, \phi, \lambda)$ and $It(\theta, \phi, \lambda)$ respectively, the reflectance $\rho(\lambda)$ and transmittance $\tau(\lambda)$ are represented by the following equations:

$$\begin{aligned} \rho(\lambda) &= \frac{1}{2\pi} \int_0^{2\pi} \int_0^{\pi/2} Ir(\theta,\phi,\lambda) \sin\theta d\theta d\phi \\ \tau(\lambda) &= \frac{1}{2\pi} \int_0^{2\pi} \int_{\pi/2}^{\pi} It(\theta,\phi,\lambda) \sin\theta d\theta d\phi \end{aligned} \quad (4)$$

Relationships between the reflectance $\rho(\lambda)$ and the aforesaid partial reflectance $r(\lambda)$, and between the transmittance $\tau(\lambda)$ and the aforesaid partial transmittance $t(\lambda)$ are represented as follows:

$$\begin{aligned} r(\lambda) &= \alpha_f \cdot \beta' r(\lambda) \cdot \rho(\lambda) \\ t(\lambda) &= \alpha_b \cdot \beta' t(\lambda) \cdot \tau(\lambda) \end{aligned} \quad (5)$$

wherein, $\alpha_f$ and $\alpha_b$ represent constants determined by the measuring device as same as the aforesaid $\alpha$, and $\beta'r(\lambda)$ and $\beta't(\lambda)$ represent coefficients relative to angular characteristics of the reflected light and transmitted light respectively decided by the condition of the target to be measured. More specifically, $\beta'r(\lambda)$ and $\beta't(\lambda)$ are represented as the following equations:

$$\left.\begin{array}{l}\beta'r(\lambda) = \dfrac{\dfrac{1}{2\pi}\displaystyle\int_{\Delta\omega f} Ir(\theta,\phi,\lambda)\sin\theta d\theta d\phi}{\dfrac{1}{2\pi}\displaystyle\int_0^{2\pi}\int_0^{\pi/2} Ir(\theta,\phi,\lambda)\sin\theta d\theta d\phi} \\[2em] \beta't(\lambda) = \dfrac{\dfrac{1}{2\pi}\displaystyle\int_{\Delta\omega b} It(\theta,\phi,\lambda)\sin\theta d\theta d\phi}{\dfrac{1}{2\pi}\displaystyle\int_0^{2\pi}\int_{\pi/2}^{\pi} It(\theta,\phi,\lambda)\sin\theta d\theta d\phi}\end{array}\right\} \quad (6)$$

wherein, $\Delta\omega f$ and $\Delta\omega b$ represent measuring solid angles on the front and back sides respectively. As obvious from these equations, $\beta'r(\lambda)$ is a ratio of the practically measurable reflected light to the whole reflected light reflected in various angles, and $\beta't(\lambda)$ is a coefficient similar to $\beta'r(\lambda)$ relative to the transmitted light. Also, from Kirchhoff's Laws $$\alpha(\lambda) = \epsilon(\lambda) \qquad (7)$$

is established, so that when $\beta r(\lambda) = \alpha_f \cdot \beta'r(\lambda)$, $\beta t(\lambda) = \alpha_b \cdot \beta't(\lambda)$ are assumed, $$\epsilon(\lambda) = 1 - r(\lambda)/\beta r(\lambda) - t(\lambda)/\beta t(\lambda) \qquad (8)$$

is established. Emissivity of the target TG may be calculated in accordance with this equation.

Next, two calculating methods for obtaining the temperature of the target TG will be explained hereinbelow.

(First Calculating Method)

If $\beta r(\lambda)$ and $\beta t(\lambda)$ are assumed to be functions including n ($n \geq 1$) unknowns and m ($m \geq 1$) unknowns respectively, the number of the unknowns together with the temperature T becomes $(n+m+1)$.

In the case where the influence of the radiated light from the surrounding-object must be taken into consideration, the following equation is obtained by transforming the equation (2).

$$\epsilon(\lambda) \times Do(\lambda, T) + \rho(\lambda) \times Df(\lambda) + \tau(\lambda) \times Db(\lambda) = D(\lambda) \qquad (2)'$$

From the equations (2)', (5) and (8), $$\{1 - r(\lambda i)/\beta r(\lambda i) - t(\lambda i)/\beta t(\lambda i)\} \times Do(\lambda i, T) + \{r(\lambda i)/\beta r(\lambda i)\} \times \qquad (9)$$

$$Df(\lambda i) + \{t(\lambda i)/\beta t(\lambda i)\} \times Db(\lambda i) = D(\lambda i)$$

$$i = 1, 2, \ldots, n + m + 1$$

Thus, if wavelengths of $(n+m+1)$ colors are used, the number of unknowns and conditional equations are coincided to give solution.

As a specific example, if $1/\beta r(\lambda i)$ and $1/\beta t(\lambda i)$ are assumed as the following lth - degree equations of wavelength:

$$1/\beta r(\lambda i) = \sum_{K=0}^{l} a_K \cdot \lambda_i^K$$

$$1/\beta t(\lambda i) = \sum_{K=0}^{l} b_K \cdot \lambda_i^K$$

and only the respective first terms thereof are taken, the equation (9) becomes the following equation (10).

$$\{1 - a_0 \cdot r(\lambda i) - b_0 \cdot t(\lambda i)\} \times Do(\lambda i, T) + a_0 \cdot r(\lambda i) \times \qquad (10)$$

$$Df(\lambda i) + b_0 \cdot t(\lambda i) \times Db(\lambda i) = D(\lambda i)$$

When eliminating $a_0, b_0$, $$\frac{A_1C_2 - A_2C_1}{A_1B_2 - A_2B_1} = \frac{A_2C_3 - A_3C_2}{A_2B_3 - A_3B_2} \qquad (11)$$

where,
$A_i = r(\lambda i) \times \{1 - Df(\lambda i)/Do(\lambda i, T)\}$
$B_i = t(\lambda i) \times \{1 - Db(\lambda i)/Do(\lambda i, T)\}$
$C_i = D(\lambda i)/Do(\lambda i, T) - 1$
$i = 1, 2, 3$ It is not possible to solve the equation (11) analytically. However, $Do(\lambda i, T)$ can be calculated in advance relative to a certain temperature T, and therefrom by employing the other measured values, left and right sides of the equation (11) are obtained. By repeating the calculations for several temperatures, a temperature T satisfying the equation (11) can be searched. The temperature T obtained thus far described can be deemed as the temperature of the target to be measured.

(Second Calculating Method)

A second calculating method is to calculate a temperature by taking errors into account from the beginning. That is, though accuracy of the calculated temperature depends on assumption of $\beta r(\lambda)$ and $\beta t(\lambda)$ of the equation (8), errors are possibly involved whatever functions relating to $\beta r(\lambda)$ and $\beta t(\lambda)$ are introduced. Also, in practice, measuring errors are inevitable in the measured values. Therefore, temperature calculation will be performed based the following conception.

A function h(T) is defined as the function which evaluates the degree of deviation between a radiated light assumed value $\epsilon(\lambda) \times Do(\lambda) + \rho(\lambda) \times Df(\lambda) + \tau(\lambda) \times Db(\lambda)$ and radiated light measured value $D(\lambda)$. The combination of unknowns which minimizes h(T) is a correct solution, and the temperature T at this time can be regarded as the temperature of the target to be measured. As a specific example, temperature calculation is performed by using wavelengths of N colors ($N \geq 3$), assuming $$1/\beta r(\lambda) = a_0$$

$$1/\beta t(\lambda) = b_0$$

and defining h(T) as a sum of squares at every wavelength of the difference between the radiated light assumed value and radiated light measured value.

$$h(T) = \sum_{i=1}^{N} \begin{pmatrix} \{(1 - a_0 \cdot r(\lambda i) - b_0 \cdot t(\lambda i)) \times Do(\lambda i, T) + \\ a_0 \cdot r(\lambda i) \times Df(\lambda i) + \\ b_0 \cdot t(\lambda i) \times Db(\lambda i) - D(\lambda i)\}/D(\lambda i) \end{pmatrix}^2 \quad (12)$$

The equation (12) is a quadratic equation of unknowns $a_0, b_0$, so that $a_0$ (=$a_0$ min) and $b_0$ (=$b_0$ min) which minimize $h(T)$ relative to a certain temperature T are $a_0$ and $b_0$ at the extreme value of $h(T)$. Accordingly, they can be obtained from equations $\partial h(T)/\partial a_0 = 0$ and $\partial h(T)/\partial b_0 = 0$.

These $a_0$ min and $b_0$ min are shown in vertical matrixes as the following equation:

$$\begin{pmatrix} a_0 \text{ min} \\ b_0 \text{ min} \end{pmatrix} = \frac{1}{\sum_{i=1}^{N} Ai^2 \cdot \sum_{i=1}^{N} Bi^2 - \left(\sum_{i=1}^{N} AiBi\right)^2} \times \quad (13)$$

$$\begin{pmatrix} \sum_{i=1}^{N} Bi^2 \cdot \sum_{i=1}^{N} AiCi - \sum_{i=1}^{N} AiBi \cdot \sum_{i=1}^{N} BiCi \\ \sum_{i=1}^{N} Ai^2 \cdot \sum_{i=1}^{N} BiCi - \sum_{i=1}^{N} AiBi \cdot \sum_{i=1}^{N} AiCi \end{pmatrix}$$

where, $$Ai = \frac{r(\lambda i)\{Do(\lambda i, T) - Df(\lambda i)\}}{D(\lambda i)}$$

$$Bi = \frac{t(\lambda i)\{Do(\lambda i, T) - Db(\lambda i)\}}{D(\lambda i)}$$

$$Ci = \frac{Do(\lambda i, T)}{D(\lambda i)} - 1$$

$a_0$ min and $b_0$ min shown in the equation (13) are substituted in the equation (12) to obtain $h(T)$.

From the standpoint of theory of errors, in order to evaluate the errors regardless of the number N of wavelengths, further a square root of least square error $h^*(T)$ as shown in the following equation (14) is calculated from $h(T)$ obtained as described heretofore.

$$h^*(t) = \sqrt{h(T)/N} \quad (14)$$

T is searched by repeating the aforesaid calculation changing T until the smallest $h^*(T)$ is obtained. The temperature which makes $h^*(T)$ minimum is outputted as the temperature of the target to be measured.

Having described the present invention as related to the embodiments, the present invention is not limited thereto, various changes and modifications are possible without departing from the scope and spirit of the invention claimed in the appended claims. For example, though an estimating function $h(T)$ is defined as the sum of squares every wavelength of the difference between the radiated light assumed value and radiated light measured value $D(\lambda)$ as shown in the equation (12), any $h(T)$ may be acceptable if it is a function for evaluating the deviation between the radiated light assumed value and radiated light measured value. For example, it may be the sum of the absolute values every wavelength of the difference between the radiated light assumed value and radiated light measured value. In that case, evaluation of errors is made as $h^*(T) = h(T)/N$ in lieu of the equation (14).

Though the embodiment shown in FIG. 1 is for three wavelengths, more than four wavelengths may be employed. In this case, the number of detectors, amplifiers and so on may just be changed.

Also, while an optical fiber FB is used for dividing light in FIG. 1, a half-mirror may be used or three optical filters may be moved in and out alternately mechanically. With respect to a light source, pulse light repeatedly emitted from a flash device may be used in place of a chopper.

What is claimed is:

1. Emissivity measuring apparatus for measuring an emissivity of a target to be measured, said emissivity measuring apparatus comprising:
   (a) light emitting means for emitting reference light having at least three wavelengths to said target to be measured;
   (b) first light measuring means for measuring the intensity of the reference light emitted by said light emitting means with respect to said at least three wavelengths to produce first signals;
   (c) second light measuring means for measuring the intensity of light reflected by said target with respect to said at least three wavelengths to produce second signals;
   (d) third light measuring means for measuring the intensity of light transmitted through said target with respect to said at least three wavelengths to produce third signals;
   (e) fourth light measuring means for measuring the intensity of light radiated by said target with respect to said at least three wavelengths to produce fourth signals; and,
   (f) calculating means for calculating an emissivity $\epsilon(\lambda)$ of said target on the basis of a reference light measured value, a reflected light measured value, a transmitted light measured value and a radiated light measured value according to the first, second, third and the fourth signals respectively with respect to each of said at least three wavelengths.

2. Emissivity measuring apparatus as claimed in claim 1, wherein said calculating means calculates the emissivity $\epsilon(\lambda)$ on the basis of the following equation;

$$\epsilon(\lambda) = 1 - r(\lambda)/\beta r(\lambda) - t(\lambda)/\beta t(\lambda)$$

wherein;
   $\lambda$ represents a wavelength;
   $r(\lambda)$ represents a partial reflection information as to the second signals at the wavelength $\lambda$;
   $t(\lambda)$ represents a partial transmittance information as to the third signals at the wavelength $\lambda$;
   $\beta r(\lambda)$ and $\beta t(\lambda)$ represent functions of the wavelength $\lambda$ including unknowns.

3. Pyrometer comprising;
   (a) light emitting means for emitting reference light having at least three wavelengths to said target to be measured;
   (b) first light measuring means for measuring the intensity of the reference light emitted by said light emitting means with respect to said at least three wavelengths to produce first signals;
   (c) second light measuring means for measuring the intensity of light reflected by said target with respect to said at least three wavelengths to produce second signals;

(d) third light measuring means for measuring the intensity of light transmitted through said target with respect to said at least three wavelengths to produce third signals;

(e) fourth light measuring means for measuring the intensity of light radiated by said target with respect to said at least three wavelengths to produce fourth signals; and, (f) calculating means for calculating a temperature of said target on the basis of a reference light measured value, a reflected light measured value, a transmitted light measured value and a radiated light measured value according to the first, second, third and fourth signals respectively with respect to each of said at least three wavelengths.

4. Pyrometer as claimed in claim 3, wherein said calculating means includes emissivity calculating means for calculating an emissivity $\epsilon(\lambda)$ of said target from the reference light measured value, reflected light measured value and transmitted light measured value at each of said at least three wavelengths, and includes temperature calculating means for calculating the temperature of said target on the basis of the calculated emissivity and the radiated light measured value.

5. Pyrometer as claimed in claim 4, wherein said emissivity calculating means calculates the emissivity $\epsilon(\lambda)$ on the basis of the following equation;

$$\epsilon(\lambda) = 1 - r(\lambda)/\beta r(\lambda) - t(\lambda)/\beta t(\lambda)$$

wherein;

$\lambda$ represents a wavelength;

$r(\lambda)$ represents a partial reflection information as to the second signals at the wavelength $\lambda$;

$t(\lambda)$ represents a partial transmittance information as to the third signals at the wavelength $\lambda$;

$\beta r(\lambda)$ and $\beta t(\lambda)$ represent functions of the wavelength $\lambda$ including unknowns.

6. Pyrometer as claimed in claim 3, further comprising supplying means for supplying a surrounding-object radiated light value of light coming from the surroundings of said target, and wherein said calculating means includes temperature calculating means for calculating the temperature of said target, on the basis of the respective measured values according to the first to fourth signals and the surrounding-object radiated light value supplied from said supplying means with respect to each of said at least three wavelengths.

7. Pyrometer as claimed in claim 6, wherein said calculating means includes emissivity calculating means for calculating the emissivity $\epsilon(\lambda)$ from the reference light measured value, reflected light measured value, transmitted light measured value and radiated light measured value at each of said at least three wavelengths, and said temperature calculating means calculates the temperature of said target on the basis of said calculated emissivity.

8. Pyrometer as claimed in claim 7, wherein said emissivity calculating means calculates the emissivity $\epsilon(\lambda)$ on the basis of the following equation;

$$\epsilon(\lambda) = 1 - r(\lambda)/\beta r(\lambda) - t(\lambda)/\beta t(\lambda)$$

wherein;

$\lambda$ represents a wavelength;

$r(\lambda)$ represents a partial reflection information as to the second signals at the wavelength $\lambda$;

$t(\lambda)$ represents a partial transmittance information as to the third signals at the wavelength $\lambda$;

$\beta r(\lambda)$ and $\beta t(\lambda)$ represent functions of the wavelength $\lambda$ including unknowns.

9. Pyrometer as claimed in claim 8, wherein said calculating means calculates (n+m+1) unknowns consisting of the temperature T of said target and (n+m) unknowns included in $\beta r(\lambda)$ and $\beta t(\lambda)$ representing functions of wavelength $\lambda$ including n unknowns and m unknowns respectively, by using the following (n+m+1) equations;

$$\epsilon(\lambda i) \times Do(\lambda i, T) + \{r(\lambda i)/\beta r(\lambda i)\} \times Df(\lambda i) + \{t(\lambda i)/\beta t(\lambda i)\} \times Db(\lambda i) = D(\lambda i)$$

$i = 1,2,3,\ldots, n + m + 1$ $n \geq 1, m \geq 1$ wherein;

Do($\lambda$i, T) represents a radiated light measured value of a blackbody at a temperature T with respect to a wavelength $\lambda$i;

D($\lambda$i) represents a radiated light measured value with respect to the wavelength $\lambda$i;

Df($\lambda$i) represents a front-side surrounding-object radiated light value with respect to the wavelength $\lambda$i;

Db($\lambda$i) represents a back-side surrounding-object radiated light value with respect to the wavelength $\lambda$i.

10. Pyrometer as claimed in claim 8, wherein said temperature calculating means calculates the temperature of said target in a manner that it obtains minimum value of a function which evaluates the deviation between the radiated light measured value D($\lambda$i) and a radiated light assumed value $\epsilon(\lambda i) \times Do(\lambda i, T) + \{r(\lambda i)/\beta r(\lambda i)\} \times Df(\lambda i) + \{t(\lambda i)/\beta t(\lambda i)\} \times Db(\lambda i)$ calculated from the respective measured values, the calculated emissivity and the surrounding-object radiated light value; wherein;

Do($\lambda$i, T) represents a radiated light measured value of a blackbody at a temperature T with respect to a wavelength $\lambda$i;

D($\lambda$i) represents a radiated light measured value with respect to the wavelength $\lambda$i;

Df($\lambda$i) represents a front-side surrounding-object radiated light value with respect to the wavelength $\lambda$i;

Db($\lambda$i) represents a back-side surrounding-object radiated light value with respect to the wavelength $\lambda$i.

11. Pyrometer as claimed in claim 6, wherein said supplying means includes means for measuring the intensity of light coming from the surroundings of said target with respect to said at least three wavelengths to produce the surrounding-object radiated light value.

12. Pyrometer as claimed in claim 6, wherein said supplying means includes means for inputting the surrounding-object radiated light value to said calculating means in the case where the surrounding-object radiated light value at each of said at least three wavelengths is known.

* * * * *